United States Patent [19]

Henry

[11] 4,079,149

[45] Mar. 14, 1978

[54] BENZYL OXIME ETHERS

[75] Inventor: Arthur C. Henry, Houston, Tex.

[73] Assignee: Shell Oil Company, Houston, Tex.

[21] Appl. No.: 811,645

[22] Filed: Jun. 30, 1977

[51] Int. Cl.² .................... A61K 31/15; C07C 131/00
[52] U.S. Cl. .............................. 424/327; 260/566 AE
[58] Field of Search .................. 260/566 AE; 424/327

[56] References Cited

U.S. PATENT DOCUMENTS

| B 211,786 | 1/1976 | Haddock | 260/566 AE |
| 3,845,126 | 10/1974 | Giraudon et al. | 260/566 AE |

FOREIGN PATENT DOCUMENTS

| 1,443,555 | 7/1976 | United Kingdom | 260/566 AE |
| 964,721 | 7/1964 | United Kingdom | 260/566 AE |
| 967,351 | 8/1964 | United Kingdom | 260/566 AE |

*Primary Examiner*—Gerald A. Schwartz

[57] ABSTRACT

Insecticidal benzyl oxime ethers of the formula:

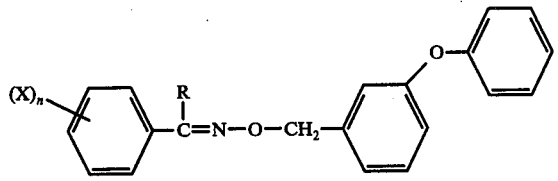

wherein the symbols have meanings defined in the specification.

8 Claims, No Drawings

BENZYL OXIME ETHERS

DESCRIPTION OF THE INVENTION

It has been found that useful insecticidal properties are possessed by benzyl oxime ethers of the formula

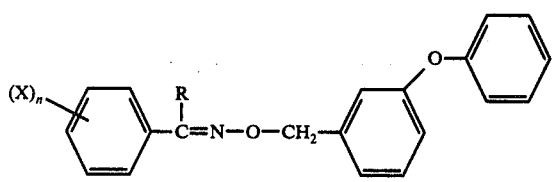

wherein n is 0, 1 or 2, X is halogen, or is alkyl, or alkoxy of from one to three carbon atoms, and R is alkyl or alkenyl of from two to seven carbon atoms, optionally substituted by from one to a plurality of halogen atoms, or is cyclopropyl, optionally substituted by from one to four methyl groups and one or two halogen atoms. In these compounds, each alkyl and alkenyl moiety is either straight-chain or branched-chain in configuration. Any halogen present preferably is lower halogen — i.e., chlorine, bromine, or fluorine.

The subgenus of these compounds in which R is cyclopropyl appears to have a particularly attractive spectrum of insecticidal activity; therefore this subgenus constitutes a preferred aspect of this invention. Of this subgenus, three preferred individual species, because of their activity, are those wherein, respectively, n is 1 and X is bonded to the carbon atom at the 4-position of the ring and is lower halogen.

For illustration, preparation of typical individual species of the genus defined by Formula I are described in the examples included hereinafter. Other typical individual species of the genus are the following, wherein the respective moieties, referring to Formula I, are:

| n | X | R |
|---|---|---|
| 1 | 4-chlorine | isopropenyl |
| 1 | 4-chlorine | dichloromethyl |
| 1 | 4-chlorine | trichloromethyl |
| 1 | 4-chlorine | 1-chloroethyl |
| 1 | 4-chlorine | 2,2,3,3-tetramethyl cyclopropyl |
| 1 | 4-chlorine | 2,2-dimethylcyclopropyl |
| 2 | 3,4-dichlorine | cyclopropyl |
| 1 | 3-chlorine | cyclopropyl |
| 1 | 4-methyl | cyclopropyl |

Compounds of Formula I can exist in the form of geometric isomers, referring to the spatial relationship of the substituents about the oxime double bond, these isomers being designated as the Z and E forms. It has been found that the E form of these compounds is significantly more active insecticidally than the Z form. Therefore, the E form, and mixtures of significant amounts thereof with the Z form, constitute a preferred aspect of the invention.

Compounds of Formula I can be prepared by effecting reaction between an alkali metal salt of the appropriate ketoxime and 3-phenoxybenzyl bromide. This reaction can be effected in some cases by treating a stirred mixture of the appropriate oxime and 3-phenoxybenzyl bromide in a solvent, such as tetrahydrofuran, or acetonitrile, or dimethylformamide in toluene, with sodium hydride. The reaction suitably can be conducted at or somewhat above room temperature, for example 15°-70° C. Since the reaction generally is exothermic, it usually will be found desirable to add the sodium hydride slowly, cooling the reaction mixture as necessary to maintain its temperature at the desired level. In some cases, it may be found to be desirable to first form the metal salt by treatment of the oxime with the hydride, and then bring the salt and the bromide together, suitably at temperatures of about 100°-110° C. In other cases, the reaction can be effected by treating a mixture of the oxime and an alkali metal base, such as potassium hydroxide, in water, with a solution of the bromide in a water-immiscible solvent, such as toluene, in the presence of a suitable phase transfer catalyst. The catalyst can be any compound which will accelerate interphase reactions in two-phase systems. Tetrabutylammonium bromide is an example. Temperatures of about 80°-100° C are suitable. In some case, the desired product can be recovered by filtering the by-product sodium or potassium bromide, evaporating the solvent from the filtrate, then employing conventional techniques, such as selective extraction, recrystallization and/or chromatography, to isolate the product. In other cases, the desired product can be recovered by extracting the crude reaction mixture with a suitable water-immiscible solvent, then isolating the product by conventional techniques.

3-phenoxybenzyl bromide is a known compound: Belgian Pat. No. 809,867.

The precursor oximes can be prepared by procedures set forth in Organic Syntheses, Collective Volume 2, pages 70-72, by mixing the appropriate ketone with hydroxylamine hydrochloride in a solvent such as aqueous methanol or ethanol, then treating the mixture with sodium hydroxide at room temperature or somewhat above, treating the resulting mixture with dilute hydrochloric acid, and recovering the oxime by conventional techniques. Alternatively, a nitrogen base, such as pyridine, can be used in place of the sodium hydroxide.

The precursor ketones can be prepared by suitable conventional methods, such as Friedel-Crafts acylation of the appropriate benzene, $(X)_n$-benzene, with the appropriate acid chloride, RC(O)Cl, using aluminum trichloride as catalyst or by treating a Grignard reagent of the appropriate R-bromide with the appropriate $(X)_n$ benzonitrile in the presence of ether as solvent at a temperature of from about 20° C to reflux, then treating the resulting mixture with dilute sulfuric acid, recovering the desired product by conventional means.

These procedures for preparing compounds of this invention are illustrated in Examples 1-10, following. In all cases, the identities of the products, and of the precursors involved were confirmed by appropriate chemical and spectral analyses.

In Examples 1 and 4, the relative proportions of the isomers in the product were not determined.

EXAMPLE 1

2-methyl-1-phenyl-1-propanone, O-(3-phenoxyphenylmethyl)oxime      (1)

3.2 g of isobutyrophenone oxime (Beilstein 7, 316; Berichte, 20, 506), 5.2 g of 3-phenoxybenzyl bromide and 30 ml of tetrahydrofuran were mixed, and then 0.9 g of sodium hydride was added. The mixture was stirred at room temperature for 18 hours, then refluxed for 2 hours, and filtered, and the filtrate was stripped of solvent. The liquid residue was chromatographed over silica gel, methylene chloride being used as eluent, to give 1, as a straw-colored liquid, boiling point not determined.

EXAMPLE 2

1-(4-chlorophenyl)-2-methyl-1-propanone,
O-(3-phenoxyphenylmethyl)oxime    (2)

133 g of aluminum chloride and 400 ml of chlorobenzene were mixed, and at room temperature 106 g of isobutyryl chloride was added drop-by-drop over a 7-minute period, with cooling to maintain the reaction mixture temperature. The mixture was stirred for 5 hours at room temperature, then poured into an ice/water mixture. The resulting mixture was extracted with methylene chloride; the extract was washed with water, dried ($MgSO_4$) and stripped of solvent under reduced pressure. The liquid residue was distilled to give 4-chloroisobutyrophenone, (2A), as a liquid, b.p.: 101°, 0.2 Torr.

91 g of 2A, 200 ml of ethanol and 40 ml of water were mixed, 60 g of hydroxylamine hydrochloride was added and then 110 g of sodium hydroxide was added over a 10-minute period. The mixture was stirred at room temperature for 1.5 hours, then at reflux for 0.5 hour, cooled, added to cold dilute hydrochloric acid and filtered. The filtrate was dried ($MgSO_4$) and stripped of solvent. The solid residue was crystallized from hexane containing a trace of ether to give 1-(4-chlorophenyl)-2-methyl-1-propanone oxime (2B), m.p.: 91°–117°.

3.86 g of 2B, 5.2 g of 3-phenoxybenzyl bromide and 30 ml of tetrahydrofuran were mixed and 0.9 g of sodium hydride was added. The mixture was heated to 37°. The mixture was cooled, stirred at room temperature for 21 hours, then filtered, and the solvent was stripped from the filtrate. The liquid residue was chromatographed (silica gel, 1/2 v/v methylene chloride/pentane) to give 2, 40% E isomer, 60% Z isomer, as a light yellow liquid, boiling point not determined.

EXAMPLE 3

1-(4-bromophenyl)-2-methyl-1-propanone,
O-(3-phenoxyphenylmethyl)oxime    (3)

26.8 g of aluminum chloride and 100 ml of bromobenzene were mixed, then 21.2 g of isobutyryl chloride was added drop-by-drop, the mixture being held at about 20°. The mixture was stirred for 17 hours at room temperature and then poured into an ice/water mixture. The mixture was extracted with methylene chloride and the extract phase was dried ($MgSO_4$) and stripped of solvent under reduced pressure. The residue was distilled to give 4-bromoisobutyrophenone, (3A), b.p.: 82°–83°, 0.02 Torr.

14.0 g of 3A, 5 ml of water, 25 ml of methanol and 7.45 g of hydroxylamine hydrochloride were mixed. 13.6 g of sodium hydroxide was added. The mixture was refluxed for 70 minutes, cooled, poured into cold dilute hydrochloric acid, and filtered. The solid product was dissolved in methylene chloride, dried ($MgSO_4$) and stripped of solvent. Recrystallization of the solid product from hexane gave 1-(4-bromophenyl)-2-methyl-1-propanone oxime (3B) m.p.: 126.5°–135.5°.

4.85 g of 3B, 5.25 g of 3-phenoxybenzyl bromide and 50 ml of tetrahydrofuran were mixed. 0.53 g of sodium hydride was added to the stirred mixture at room temperature. Heat of reaction raised the mixture temperature to about 35°. The mixture was refluxed for 2.5 hours, then filtered. The filtrate was stripped of solvent. The resulting liquid product was dissolved in methylene chloride; the solution was washed with water, dried ($MgSO_4$) and stripped of solvent. The liquid product was chromatographed over silica gel, using pentane/methylene chloride as eluent, to give 3, 33% E isomer, 67% Z isomer, as a yellow-tinted liquid, boiling point not determined.

EXAMPLE 4

1-(4-chlorophenyl)-1-propanone,
O-(3-phenoxyphenylmethyl)oxime    (4)

33.6 g of p-chloropropiophenone was mixed with 200 ml of ethanol and 40 ml of water. 24 g of hydroxylamine hydrochloride was added. 44 g of solid sodium hydroxide was added over a 10-minute period to the stirred mixture at room temperature. The mixture was heated to 80°, then refluxed for 80 minutes. The mixture was cooled and poured into cold dilute hydrochloric acid. The resulting mixture was filtered. The solid product was dissolved in methylene chloride; the solution was dried ($MgSO_4$) and stripped of solvent. Recrystallization of the solid product from hexane gave 1-(4-chlorophenyl)-1-propanone oxime (4A), m.p.: 56°–57.5°.

3.7 g of 4A, 5.2 g of 3-phenoxybenzyl bromide and 50 ml of ether were mixed. 0.53 g of sodium hydride was added the mixture was stirred for 2 days at room temperature and then refluxed for 3 hours. 50 ml of tetrahydrofuran was added and the mixture was refluxed for 24 hours, cooled and filtered. The filtrate was stripped of solvent, the liquid residue was dissolved in methylene chloride, and the solution was washed with water, dried ($MgSO_4$) and stripped of solvent. The liquid residue was chromatographed (silica gel, pentane/methylene chloride) to give 4, as a yellow liquid, boiling point not determined.

EXAMPLE 5

2-methyl-1-(4-methylphenyl)-1-propane,
O-(3-phenoxyphenylmethyl)oxime    (5)

24.6 g of 2-bromopropane was added to a mixture of 4.8 g of magnesium, a few crystals of iodine, and 200 ml of ether. To the resulting Grignard reagent was added a solution of 23.4 g of p-tolunitrile in ether, over a 15-minute period at about 30°. The mixture was stirred at room temperature for 32 hours and refluxed for 3 days, then treated with dilute sulfuric acid, cooled and extracted with ether. The ether solution was dried ($MgSO_4$) and stripped of solvent. The resulting liquid product was cooled, unreacted starting material was decanted. The residue was chromatographed (silica gel, methylene chloride) to give 1-(4-methylphenyl)-2-methyl-1-propanone (5A).

3.2 g of 5A, 7.4 g of hydroxylamine hydrochloride, 40 ml of ethanol and 80 ml of water were mixed. 4.4 g of sodium hydroxide was added to the stirred mixture at room temperature. The mixture was stirred for 4 hours at reflux temperature, cooled, poured into cold dilute hydrochloric acid and extracted with methylene chloride. The extract was dried ($MgSO_4$) and stripped of solvent and the product was chromatographed (silica gel, methylene chloride/ether) to give 1-(4-methylphenyl)-2-methyl-1-propanone oxime (5B), as a liquid, boiling point not determined.

0.7 g of 5B, 1.05 g of 3-phenoxybenzyl bromide and 20 ml of tetrahydrofuran were mixed and at room temperature, 0.114 g of sodium hydride was added. The mixture was stirred at room temperature for 40 hours. The solvent was stripped, the residue was dissolved in methylene chloride, the solution was washed with water, dried ($MgSO_4$), and the liquid product was chromatographed (silica gel, 50/50 by volume mixture of methylene chloride and pentane) to give 5, as a yellow liquid, containing equal amounts of the E and Z isomers.

EXAMPLE 6

1-(4-fluorophenyl)-2-methyl-1-propanone, O-(3-phenoxyphenylmethyl)oxime (6)

1.8 g of 1-(4-fluorophenyl)-2-methyl-1-propanone oxime in 10 ml of 20% dimethylformanide in toluene was added to 0.5 g of sodium hydride (1.0 of a 50% dispersion in oil) in 20 ml of 20% dimethylformamide in toluene at 70°-80° over a 10-minute period. A solution of 2.9 g of 3-phenoxybenzyl bromide in 15 ml of 20% dimethylformamide in toluene was added over a 5-minute period. The mixture was stirred at 100°-110° for 3 hours, and then was cooled to room temperature. 5 ml of methanol was added and the mixture was poured onto a mixture of ice and hydrochloric acid. The resulting mixture was extracted with diethyl ether. The extract was washed with 10% sodium bicarbonate solution, and dried ($Na_2SO_4$). The solvent was evaporated and the residue was chromatographed on silica gel using toluene as eluent. Two fractions were obtained. After removal of the solvent, the first fraction was an oil, (6A), identified as a 3:1 mixture of the E and Z isomers of 6, n22D (refractive index) = 1.5740.

On removal of solvent from the second fraction, an oil (6B) was obtained and identified as a 1:1 mixture of the E and Z isomers of 6, n22D = 1.5712.

EXAMPLE 7

1-(4-fluorophenyl)-2-methyl-1-propanone, O-(3-phenoxyphenylmethyl)oxime (7)

This compound was prepared as an oil, 95% Z isomer, 5% E isomer, n22D = 1.5688, from the Z isomer of 1-(4-fluorophenyl)-2-methyl-1-propanone oxime and 3-phenoxybenzyl bromide, by the general procedure described in Example 1.

EXAMPLE 8 cyclopropyl(4-fluorophenyl)methanone, O-(3-phenoxyphenylmethyl)oxime (8)

A mixture of 2.4 g of cyclopropyl(4-fluorophenyl) methanone oxime, 50 ml of dry acetonitrile and 0.64 g of a 50% dispersion of sodium hydride in mineral oil was stirred at room temperature for 2 hours. 3.5 g of 3-phenoxybenzyl bromide was added and the mixture as refluxed for 3 hours. The mixture then was cooled, and filtered and the solvent was evaporated. The residue was dissolved in ether, the solution was washed, in sequence, with 7% sulfuric acid solution, 10% sodium bicarbonate solution, and water, then dried ($Na_2SO_4$) and the solvent was evaporated. The residue was chromatographed on silica gel in hexane, using a 4/1 by volume mixture of toluene and hexane as eluent, to give 8, 95% E isomer, 5% Z isomer, as a colorless oil.

EXAMPLE 9 cyclopropyl(2,4-diphenylmethyl)methanone, O-(3-phenoxyphenylmethyl)oxime (9)

9 was prepared as a colorless oil (45% E isomer, 55% Z isomer, from cyclopropyl 2,4-xylyl ketoxime by the procedure described in Example 8.

EXAMPLE 10

(4-chlorophenyl)cyclopropylmethanone, O-(3-phenoxyphenylmethyl)oxime (10)

10 was prepared by the procedures described in Example 6. The product was chromatographed on silica gel, using toluene as eluent. Two fractions were obtained: the first (10A), essentially 100% E-isomer; (n22D = 1.6078) the second, (10B), a 1:1 mixture of the E and Z isomers (n22D = 1.6059), From these the Z isomer, (10C), was isolated.

EXAMPLES 11-16

By the procedures set forth in Examples 1-10, the following further individual species of the genus of Formula I wherein R = cyclopropyl were prepared:

| Ex. No. | Compound No. | n | X | Isomeric Form | n22D | |
|---|---|---|---|---|---|---|
| 11 | 11 | 0 | — | — | | |
| 12 | 12 | 1 | 4-Br | 95%E | 1.6209 | $(n_D{}^{17})$ |
| 13 | 13 | 1 | 4-(tert-butyl) | 95%E | 1.5872 | |
| 14 | 14 | 1 | 4-$CH_3O$— | 95%E | 1.5934 | |
| 15 | 15 | 2 | 3,4-$(CH_3)_2$ | 95%E | 1.5933 | |
| 16 | 16 | 1 | 4-$C_2H_5$— | 70%E | 1.5939 | |

The compounds of this invention exhibit useful insecticidal, tickicidal and acaricidal activity, being of particular interest for control of the larval "caterpillar" or "worm" forms of lepidopterous insects of the genus Heliothis, such as *H. zea* (corn earworm, cotton bollworm, tomato fruitworm), *H. virescens* (tobacco budworm); the genus Agrotis, such as *A. ipsilon* (black cutworm); the genus Trichoplusia, such as *T. ni* (cabbage looper), and the genus Spodoptera, such as *S. littoralis* (Egyptian cotton leafworm).

The activity of Compounds 1 - 5, 6A, 7, 10A, 10B and 12-16 with respect to insects and acarids was determined by using standardized test methods to establish the $LC_{50}$ dosage (in milligrams of test compound per 100 milliliters of solvent or liquid carrier required in the solution or suspension of test compound used) that was required to kill 50% of the test insects. The test insects were the housefly, corn earworm, pea aphid and 2-spotted mite. Activity with respect to mosquito larvae was determined by placing the larvae in water containing the test compound.

With respect to houseflies, compounds 1-5, 6B and 7 were found to be slightly active, while compounds 10A and 10B were found to be moderately active.

With respect to the aphids, compounds 1-5, 6B and 7 were found to be slightly active, which compounds 10A and 10B were found to be moderately active.

With respect to mosquito larvae, compounds 1, 3-5, 6B and 7 were found to be inactive or slightly active, and compounds 2 and 10B were moderately active and compound 10A was highly active.

With respect to the corn earworms, compounds 1-5, 6B, 7, 8, 11 and 13-16 were found to be moderately active, while compounds 10A, 10B and 12 were highly active.

Only compound 13 was active with respect to the mites; it was moderately active.

The insecticidal and acaricidal activity of compounds 6-16 also was determined by similar standardized test methods with respect to mustard beetles, vetch aphids, glasshouse spider mites and Egyptian cotton leafworms.

With respect to the mustard beetle, compounds 6A, 6B, 10A, 10B, 10C, 12–14 and 16 were moderately active.

With respect to the cotton leafworm, compounds 7 and 9 were slightly active, compounds 6A, 6B, 10C, 11, 13 and 14–16 were moderately active, while compounds 8, 10A, 10B and 12 were highly active.

With respect to vetch aphid, compounds 6A, 6B, 7, 9, 10B and 10C were inactive or very slightly active, compounds 8 and 11 were slightly active, and compounds 10C and 12–16 were moderately active.

With respect to the mites, compounds 6A, 6B, 8, 9, 10C, 11, 12, 14 and 15 were inactive or slightly active and compounds 7, 10A, 10B, 13 and 16 were moderately active.

Activity of compounds of Formula I also were tested for activity with respect to ticks, *Boophilus microplus*, as follows: the compound to be tested was formulated as a solution or fine suspension in acetone containing 10% by weight of polyethylene glycol having an average molecular weight of 400. The formulation contained 0.1% by weight of the compound to be tested. One milliliter of the solution or suspension was applied evenly to a filter paper situated inside a petri dish. After the paper was sufficiently dry it was folded in half and partly crimped along the outer edge to form a packet. About 80–100 larval ticks were transferred into the packet which was then sealed completely. The packets were placed inside an incubator, maintained at 27° C and 80% relative humidity, before assessing mortality 24 hours later.

Compounds 6A, 6B, 7, 9, 10A, 10B and 12–16 were found to be slightly active, and compounds 8, 10C and 11 were found to be moderately active.

The invention includes within its scope a carrier, optionally a surface-active agent — and, as active ingredient, at least on pesticide of this invention. Likewise the invention includes also a method of combatting pests at a locus which comprises applying to the locus an effective amount of at least one pesticide of the invention.

The term "carrier" as used herein means a material which may be inorganic or organic and of synthetic or natural origin with which the active compound is mixed or formulated to facilitate its application to the plant, seed, soil, animal or other object to be treated, or its storage, transport or handling. The carrier may be solid or a liquid.

Suitable solid carriers may be natural and snythetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example, superphosphates.

Suitable liquid carriers include solvents for the pesticides of this invention and liquids in which the pesticide is insoluble or only slightly soluble.

Examples of such solvents and liquid carriers generally are water, alcohols, for example, isopropyl alcohol; ketones, such as acetone, methyl ethyl ketone, methyl isobutyl ketone and cyclohexanone; ethers; aromatic hydrocarbons such as benzene, toluene and xylene; petroleum fractions, such as kerosene, light minerals oils; chlorinated hydrocarbons, such as carbon tetrachloride, perchlorethylene, trichloroethane; including liquified normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bain formulations. Wettable powders are usually compounded to contain 25, 50 or 75%w of toxicant and usually contain, in addition to solid carrier, 3–10%w of stabilizer(s) and/or other additives such as penetrants or stickers. Dusts are usually formulated as a dust concentrate having a similar composition to that of a wettable powder, but without a dispersant, and are diluted in the field with further solid carrier to give a composition usually containing ½–10%w of active ingredient. Granules may be manufactured by agglomeration or impregnation techniques. Generally, granules will contain ½–25%w active ingredient and 0–10%w of additives such as stabilizers, slow release modifiers and binding agents. Emulsifiable concentrates usually contain, in addition to the solvent, and when necessary, co-solvent, 10–50%w/v active ingredient, 2–20%w/v emulsifiers and 0–20%w/v of appropriate additives such as stabilizers, penetrants and corrosions inhibitors. Suspension concentrates are compounded so as to obtain a stable, non-sedimenting, flowable product and usually contain 10–75%w active ingredient, 0–5%w of dispersing agents, 0.1–19%w of suspending agents such as protective colloids and thixotropic agents, 0–19%w of appropriate additives such as defoamers, corrosion inhibitors, stabilizers, penetrants and stickers, and as carrier, water or an organic liquid in which the active ingredient is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of active ingredient at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary disage of the active ingredient at the locus being within the skill of those versed in the art. In general, however, the pesticidal formulation is applied to the folage of the plants, or to the hair, fur or skin of the animal to be protected to provide the effective dosage of the compound of this invention at the locus to be protected — i.e., the dosage to which the pest contacts — is of the order of 0.001% to 0.5% based on the total weight of the formulation, through under some circumstances the effective concentration will be as little as 0.001% or as much as 2%, on the same basis.

I claim:

1. The E isomeric form of a compound of the formula

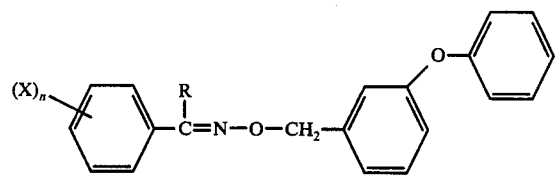

wherein $n$ is 0, 1 or 2, X is lower halogen, or is alkyl or alkoxy of from one to three carbon atoms, and R is alkyl or alkenyl of from two to seven carbon atoms, optionally substituted by from one to a plurality of halogen atoms, or is cyclopropyl, optionally substituted by from one to four methyl groups and/or one or two halogen atoms.

2. A compound according to claim 1 wherein R is cyclopropyl.

3. A compound according to claim 2 wherein $n$ is one, X is bonded to the carbon atom at the 4-position in the ring, and is lower halogen.

4. A compound according to claim 3 wherein X is fluorine.

5. A compound according to claim 3 wherein X is chlorine.

6. A compound according to claim 3 wherein X is bromine.

7. A pesticidal composition comprising an effective amount of a compound of claim 1, together with a carrier and optionally a surface-active agent.

8. A method for killing insects, acarids and ticks which comprises applying to a locus to be protected an effective amount of a compound of claim 1.

* * * * *